United States Patent [19]

Cooney et al.

[11] 4,395,490
[45] Jul. 26, 1983

[54] PROCESS FOR PRODUCTION OF IMPROVED MALTASE

[75] Inventors: Charles L. Cooney, Brookline; Eugene J. Schaefer, Somerville, both of Mass.

[73] Assignee: Massachusetts Institute of Technology, Cambridge, Mass.

[21] Appl. No.: 329,449

[22] Filed: Dec. 10, 1981

Related U.S. Application Data

[63] Continuation-in-part of Ser. No. 177,709, Aug. 13, 1980, Pat. No. 4,332,899.

[51] Int. Cl.$^3$ .......................... C12N 9/26; C12N 1/16
[52] U.S. Cl. .................................... 435/201; 435/940; 435/255
[58] Field of Search ............................... 435/201, 172

[56] References Cited

U.S. PATENT DOCUMENTS 4,071,407  1/1978  Hall ................................ 435/201 X
4,081,326  3/1978  Hall ................................ 435/201 X

*Primary Examiner*—Lionel M. Shapiro
*Attorney, Agent, or Firm*—Arthur A. Smith, Jr.; Paul J. Cook

[57] ABSTRACT

Maltase is produced by growing a mutant of the yeast strain *Saccharomyces italicus* capable of growing in a growth medium utilizing sucrose as the carbon source. Maltase production is optimized by controlling time of fermentation, growth medium composition and sonication time during maltase recovery.

8 Claims, 7 Drawing Figures

PROCESS FOR PRODUCTION OF IMPROVED MALTASE

This application is a continuation-in-part of co-pending application, Ser. No. 177,709, filed Aug. 13, 1980, now U.S. Pat. No. 4,332,899 issued June 1, 1982.

BACKGROUND OF THE INVENTION

This invention relates to a process for producing maltase therewith utilizing, as a carbon source, sucrose.

Maltase (α-glucosidase, EC 3.2.1.20) is an enzyme presently used in clinical assays for amylase. The maltase is utilized in an intermediate reaction wherein maltose, formed by the action of amylase on an oligosaccharide, is converted to glucose. The glucose is subsequently measured to determine the amylase activity. Presently, maltase is produced from yeast strains such as *Saccharomyces cerevisae* or *Saccharomyces italicus*. The maltase produced from *Saccharomyces italicus* is particularly useful in the assay for amylase in that it will not degrade higher oligosaccharides. Unfortunately, the carbon source in the growth medium for *Saccharomyces italicus* is maltose which is very expensive as compared to possible alternative carbon sources. Attempts to substitute relatively inexpensive sucrose or glucose as the carbon source have proven ineffective with *Saccharomyces italicus*, since regulatory controls in the yeast cells block maltase production when utilizing any other carbon source. Also contaminating amounts of glucose sometimes present in commercial batches of maltose can have a deleterious effect on maltase production. In addition, the use of maltose as a carbon source has presented production difficulties since the activity of the maltase produced peaks just before the maltose in the medium is depleted thereby requiring that the cells be harvested within a relatively narrow time span.

Accordingly, it would be desirable to provide a means for producing maltase useful in clinical assays for amylase from a yeast strain which does not require maltose as the carbon source. Furthermore, it would be desirable to provide such a means which permits the use of inexpensive sucrose as the carbon source. Furthermore, it would be desirable to provide such a means wherein the activity of the maltase produced is not sharply reduced within a short time span so that the timing of cell harvesting is far less critical than in presently available processes. In addition, it would be desirable to provide such a means wherein the stability and yield of maltase can be optimized.

SUMMARY OF THE INVENTION

In accordance with this invention, maltase enzyme is produced from a new strain of yeast comprising mutants of *Saccharomyces italicus*, which, unlike the parent strain, will grow and produce maltase in a medium wherein the carbon source need not be maltose and can include sucrose as the carbon source. Stability of the maltase produce is improved by controlling time of fermentation while maltase yield is improved by adding a small amount of yeast extract to the growth medium and by controlling sonication time during maltase recovery.

DESCRIPTION OF THE SPECIFIC EMBODIMENTS

The strain of yeast utilized in the present invention is produced by mutation of *Saccharomyces italicus* with a mutagenic agent such as ultraviolet light, nitroso-guanidine, ethyl methanesulfonate or other known agents. The novel microorganisms of this invention are strains of *Saccharomyces italicus* which exhibit the following characteristics.

The yeast strains utilized in this invention will grow and produce maltase in a growth medium which can contain, as the carbon source, sucrose. Thus, the strains of yeast utilized in the present invention differ from presently available *Saccharomyces italicus* which are not capable of utilizing sucrose as a carbon source. This strain is also unique in that it produces maltase in the absence of the normal inducer: maltose. Alternative carbon sources which can be utilized by the strain of yeast in this invention include maltose, glycerol, acetate, fructose and glucose. The carbon source is present in the growth medium at concentrations between about 5 g/l and about 60 g/l. For example, with sucrose, the growth medium can contain the sucrose at a concentration of between about 5 and about 50 g/l, preferably between about 40 and about 45 g/l. The growth medium may also contain protein hydrolyzate such as Bacto-Peptone, Difco B118 and a yeast extract such as Bacto Yeast Extract, Difco B126.

In addition, the growth medium contains a source of potassium and phosphorus such as monobasic potassium phosphate or the like, a source of ammonia and sulphur, such as ammonium sulfate and a source of magnesium such as magnesium sulfate. A typical growth medium contains the yeast extract, protein, ammonium sulfate, monobasic potassium phosphate, sodium biphosphate, magnesium sulfate and the carbon source. Typically, the ammonium sulfate comprises between about 2 and about 10 g/l, the monobasic potassium phosphate comprises between about 0.5 and about 3 g/l, the magnesium sulfate comprises between about 0.5 and about 3 g/l, the yeast extract comprises between about 1 and about 15 g/l, preferably between about 2 and 5 g/l and the carbon source comprises between about 20 and about 50 g/l. Surprisingly, it has been found that when the concentration of yeast extract is controlled within the range set forth the amount of maltase that can be recovered is increased as compared to processes utilizing lesser amounts of yeast extract.

The pH of the medium generally is maintained between about 4.5 and about 6.0, preferably about 5.5. It is preferred to control the pH at 5.5 during the course of the fermentation by the addition of sodium hydroxide.

Sterile air is sparged into the fermentor at a rate sufficient to meet the needs of the yeast and typically between about 0.5 VVM and about 2.0 VVM. The growth medium is maintained at a temperature between about 22° C. and about 32° C., preferably between about 29° C. and about 31° C. An antifoam product, such as P-2000 manufactured by Dow Chemical Company, can be added at a concentration of about 0.2 ml/l to control foaming.

In accordance with this invention, it also has been found that when fermenting with sucrose in the growth medium, the maltase produced is more toward the end of fermentation. This provides greater flexibility on the part of the operator in choosing a harvest time for the fermentation.

This fermentation may also be operated in a continuous mode. In such a process, the growth medium is pumped into the fermentor at a constant flowrate and culture broth is continually removed in order to maintain a constant volume in the vessel. At steady state, the growth rate of the cells is equal to the dilution rate: the incoming flowrate divided by the total volume. One advantage of continuous culture is that the productivity is generally much higher than in the case of a batch fermentation. Another advantage in this particular case is that the maltase activity remains constant thus eliminating the need to harvest the cells within a narrow time span as in the case for batch culture.

The Cells are then harvested and the maltase enzyme is released by conventional techniques, such as rapid centrifugation followed by sonication, permeabilization or french-pressing. However, it has been found that sonication time can be controlled to optimize and maximize recovery of active maltase. In accordance with this invention, suitable sonication time is between about 1 and 6 minutes, preferably between about 2 and 4 minutes when using sonication time less than this range yield of maltase is reduced. When using sonication times greater than this range, maltase activity is reduced. The maltase then is purified such as by ion exchange chromatography, gel filtration, fractionation or the like to remove extraneous materials. The purified maltase then can be stored at low temperatures or can be lyophilized and reconstituted when used. Alternatively, the cells can be used without the recovery of maltase by employing cells of Saccharomyces italicus which have been permeabilized by treatment with agents such as dimethyl sulfoxide or toluene. Such permeabilized whole cells permit maltose conversion to glucose without recovery of maltase.

The following examples illustrate the present invention and are not intended to limit the same.

EXAMPLE I

This example illustrates the formation of a mutant of Saccharomyces italicus useful in the process of this invention. The selection of this mutant is based on the follow-conditions: the wild type Saccharomyces italicus, ATCC 22185, will not grow on sucrose because it lacks invertase, the normal sucrose-splitting enzyme; sucrose may be catabolized using maltase, but sucrose will not induce maltase formation. Thus, only a mutant which constitutively produces maltase will be able to grow on sucrose. Such a mutant could be generated with one of many well-known mutagenic agents such as ultraviolet light, nitroso-guanidine and ethyl methanesulfonate. The following protocol was employed for mutagenesis with ethyl methanesulfonate and selection. An agar slant with the composition: yeast extract 10 g/l, peptone 20 g/l, glucose 20 g/l, agar 20 g/l was inoculated with the wild type Saccharomyces italicus. After 24 hours growth, the cells were suspended in 3.5 ml of pH 7.0, 1/15 molar phosphate buffer. One hundred μl of ethyl methanesulfonate was added and the suspension was shaken at 30° C. After about one hour, 1 ml of this suspension was added to 40 ml of a 5% sodium thiosulfate solution to inactivate the ethyl methanesulfonate. The cells were then harvested by centrifugation, washed twice and resuspended in a medium composed of: 10 g/l yeast extract, 20 g/l peptone, and 20 g/l glucose. After growing for several generations at 30° C., the cells were centrifuged, washed twice and resuspended in sterile distilled water. Aliquots of 0.1 ml were then plated on a medium comprised of: 6.7 g/l Yeast Nitrogen Base (Difco B391), 20 g/l sucrose, and 20 g/l agar. After 24 hours, several colonies were picked for further study. The chosen mutants were then tested in liquid medium of the same composition but without the agar. Cells were harvested after growth, sonicated and the maltase activity was assayed. All of these mutants produced maltase to some extent since the selection procedure only allows constitutive maltase producers to grow, but some synthesized much more enzyme than others. In other words, different mutational events may effect the same end result; all are constitutive producers but some are more efficient than others. The highest producing mutant of those tested was designated S. italicus ATCC 20601.

EXAMPLE II

A comparison was done of maltase production by wild type and constitutive mutants of S. italicus grown on various carbon sources. Inoculum grown on 6.7 g/l of Yeast Nitrogen Base (Difco) plus 20 g/l of glucose for 18 hours. Shake flasks containing 50 ml of a culture medium comprised of: 8.9 g/l $(NH_4)_2SO_4$, 5.7 g/l $KH_2PO_4$, 1.7 g/l $Na_2HPO_4$, 1.3 g/l $MgSO_4.7\ H_2O$, 5 g/l Yeast Extract, and 25 g/l of the carbon source (except in the case of acetate —8.2 g/l of sodium acetate was used) at pH 5.5 were started with a 10% innoculum and incubated at 30° C. The cells were harvested at mid-log phase growth and the maltase activity was assayed after sonication of the cells.

| Carbon Source | Maltase (units/gram dry cell weight) | |
|---|---|---|
| | Wild Type | Mutant |
| Sucrose | No growth | 1330 |
| Maltose | 870 | 770 |
| Glycerol | 10 | 1130 |
| Acetate | 10 | 770 |
| Fructose | 10 | 375 |
| Glucose | 10 | 320 |

Thus, the best maltase production occurs with the constitutive mutant grown on sucrose as the carbon source.

EXAMPLE III

This constitutive mutant of S. Italicus was grown in a 5-liter fermentor at 30° C., pH 5.5 (controlled by NaOH addition), and aerated at a rate of 1 VVM. Two liters of a culture medium comprised of 8.9 g/l $(NH_4)_2SO_4$, 1.65 g/l $KH_2PO_4$, 1.3 g/l $MgSO_4.7H_2O$, 0.2 g/l $CaCl_2$, 5 g/l Yeast Extract, 2.75 g/l Peptone and 50 g/l of sucrose were inoculated with 200 ml of an 18 hour culture grown on 6.7 g/l of Yeast Nitrogen Base and 40 g/l sucrose. After ten hours of growth, the cells were harvested. The cell density was 10.4 g/l and the maltase activity was 1880 units per gram dry cell weight. This yield was more than 3-fold greater than the typical volumetric yield of the present processes.

EXAMPLE IV

Maltase production by the wild type *S. italicus*, ATCC 22185, and the constitutive mutant of *S. italicus* of this invention were compared in continuous culture experiments. The culture medium for the wild type was comprised of: 30 g/l maltose, 8.9 g/l $(NH_4)_2SO_4$, 1.65 g/l $KH_2PO_4$, 1.3 g/l $MgSO_4$, $7H_2O$, 0.1 g/l $CaCl_2$, 0.2 ml/l P-2000 antifoam, 2 µg/l biotin, 400 µg/l pantothenate, 2 mg/l inositol, 400 µg/lpyridoxine, 400 µg/l thiamine, 2.78 mg/l $FeSO_4.7H_2O$, 2.88 mg/l $ZnSO_4.7H_2O$ 1.6 mg/l $CuSO_4$, $5H_2O$, 2.42 mg/l $Na_2MoO_4.2H_2O$, 2.38 mg/l $CaCl_2.6H_2O$, 1.69 $MnSO_4.H_2O$. The culture medium for the constitutive mutant was the same except that 30 g/l sucrose replaced maltose as the carbon source and the medium was supplemented with the following vitamins: 2 µg/l folic acid, 400 µg/l niacin and 200 µg/l riboflavin. All vitamins were filter sterilized separately while the rest of the components were autoclaved. Two liters of this medium were inoculated with 200 ml of an 18 hour culture of the appropriate strain grown on the same medium. The cells were grown at 30° C., pH 5.5 (controlled by NaOH addition), and aerated at 1 VVM. When the culture reached mid-long phase growth, sterile medium of the same composition was continually pumped into the fermentor and a portion of the broth was pumped out to maintain a constant volume. The growth rate of the cells was thus defined by the rate of addition of fresh medium. Several growth rates were studied for each strain and the steady state maltase activities were as follows:

| Strain | Dilution Rate $(Hr^{-1})$ | Maltase (Units/g) | Cell Mass (g/l) |
|---|---|---|---|
|  | 0.1 | 420 | 11.1 |
| Wild | 0.2 | 510 | 8.8 |
| Type | 0.3 | 410 | 3.0 |
|  | 0.4 | 410 | 2.4 |
|  | 0.06 | 1210 | 13.8 |
| Mutant | 0.12 | 1370 | 14.3 |
|  | 0.21 | 1370 | 11.9 |
|  | 0.30 | 1120 | 2.8 |

In this case, the mutant produced maltase with approximately three times the specific activity of that made by the wild type, independent of growth rate.

EXAMPLE V

This Example illustrates that when using sucrose in the growth medium, the maltose produced is more stable at the end of fermentation.

The performance of the wild type *S. italicus* in a batch fermentation on maltose provides a baseline against which future improvements may be judged. The mineral salts medium of Example IV was used with an initial maltose concentration of 45 g/liter. A liquid working volume of three liters was used with an air flow rate of 3 standard liter per minute (SLPM). The maximum agitation was limited to 1000 RPM due to mechanical difficulties. An innoculum flask was started 24 h before the start of the experiment using the same medium and a loopful of cells from an agar slant as in Example I. Four hours prior to the beginning of the fermentation, 300 ml of fresh medium was innoculated from this flask to insure that the cells innoculated into the fermentor were growing expoentially; this 300 ml culture was used to innoculate the fermentor. Samples were taken hourly for measurements of culture turbidity, maltase activity, and maltose and ethanol concentrations.

Figure 1:
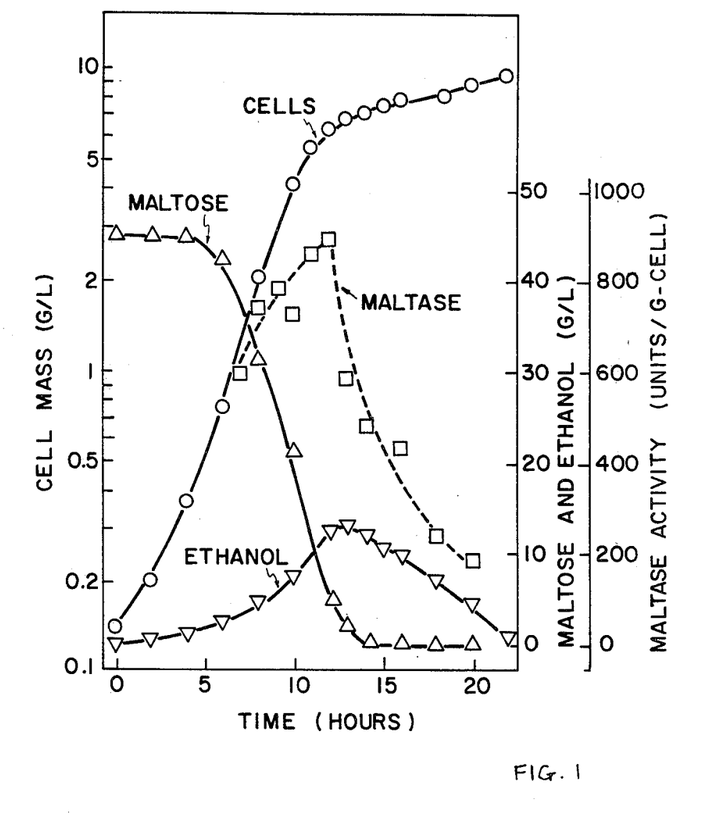
FIG. 1 is a graph of cell mass and activity versus time for batch fermentation of wild type *S. italicus* on maltase.

The results of this experiment, shown in FIG. 1, are characteristic of a typical yeast fermentation; maltose is rapidly utilized to produce cell mass and ethanol is produced in response to the well-known Crabtree effect. The formation of ethanol results in a low yeld of cells on maltose, 0.15 g cell per g maltose. During this phase of growth (0–13 h), the maximum specific growth rate is 0.45 $h^{-1}$.

The maltase specific activity is not constant during the fermentation; it passes through a maximum value of 890 units per gram dry cell weight just as the maltose is exhausted. When there is no longer any maltose in the medium, the induction of maltase ceases due to a lack of inducer and no further synthesis occurs. The specific activity then drops rapidly during subsequent growth on ethanol as the existing maltase molecules are diluted out by newly synthesized cell material. In this experiment, the specific activity decreases at a rate faster than can be ascribed to dilution by further growth. It appears that the enzyme is being inactivated or degraded while the cells are growing on ethanol. The inactivation is initially very rapid, 25% of the total activity is lost in the first hour, followed by a slower first-order decay in total activity. Less than 25% of the maximum total activity remains 10 h after exhaustion of the maltose.

The maltase activity is not constant during the first half of the fermentation either, even though maltose is in plentiful supply. One possible explanation of this behavior is that catabolite repression adversely affects maltose expression during this phase when the specific growth rate is close to its maximum value.

The constitutive mutant, (strain 1-4), did not grow well on a mineral salts medium. Above a cell concentration of about 2 g/liter the growth becomes particularly enfeebled. Thus, the usual mineral salts medium was fortified with 2 g/liter of yeast extract (Difco) in order to obtain reasonable growth in batch culture. Also, the use of a low concentration of a complex nutrient is often recommended because of its role as a chelating agent to prevent the precipitation of magnesium or trace metals during sterilization. Thus, the use of a medium containing a small amount of yeast extract may offset an increased raw materials cost with a greater ease of handling.

Figure 2:
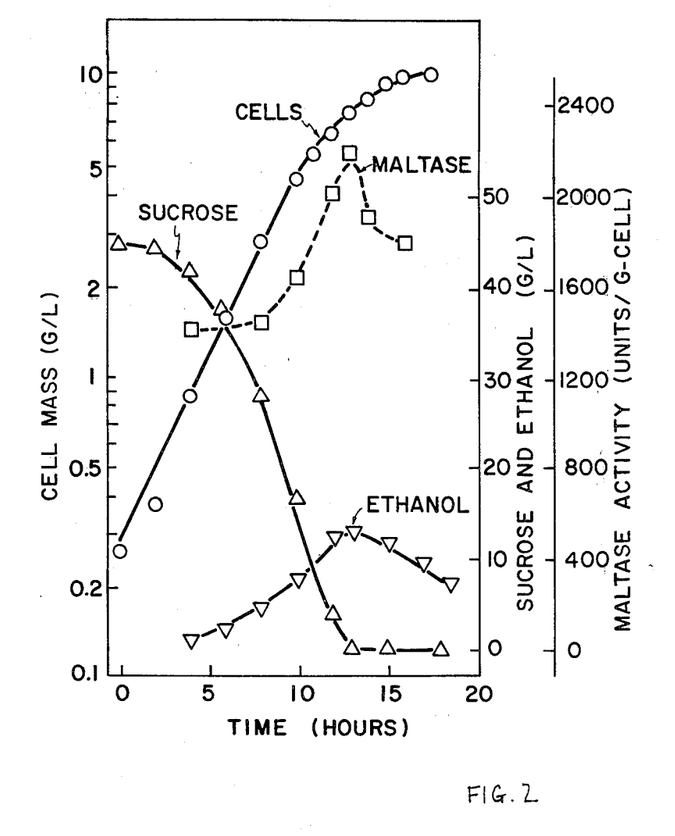
FIG. 2 is a graph of cell mass and activity versus time for batch fermentation of constitute mutant 1-4 on sucrose.

In accordance with these findings, a batch fermentation was performed using 2 liter of the mineral salts medium supplemented with 2 g/liter of Yeast Extract and deleting the vitamins. The sucrose concentration was 45 g/liter. Innoculus was grown on 200 ml of the same medium for 18 h after being started with a loopful of cells. All other procedures were performed as in previous batch fermentations. The results of this run are presented in FIG. 2. The growth behavior of this mutant is similar to that observed for the wild type. Ethanol is produced during rapid growth on sucrose and is then utilized more slowly by the cells. The maximum specific growth rate was 0.32 $h^{-1}$, slower than the wild cell type. The maltase activity peaks just as the sucrose is depleted, similar to the parent. There still seems to be some effect of catabolite repression on this system since the specific activity reaches its peak as the growth rate slows down. The degree of repression on maltase synthesis seems to be about the same as in the wild type since the extent of enzyme depression during the period of rapid growth is roughly the same in both cases (approximately 35%). However, catabolite inactivation in this mutant seems to be less of a problem than for the wild type. The total maltase activity rapidly decreased (only 25% of the maximum total activity remained after 10 h) after exhaustion of maltose. In this case, the total activity does not decrease after exhaustion of the sucrose, in fact it increases somewhat. The drop in specific activity reflects a much lower rate of maltase synthesis during growth on ethanol and the dilution of existing maltase by subsequent growth.

The most important result from this fermentation is that the maltase specific activity has more than doubled compared to the wild type, 2210 units per gram cell compared to 890 units per gram cell. This high specific activity results in a two-fold increase in specific productivity. In addition, recovery costs should decrease since fewer cells are needed to obtain the same amount of maltase. Also, by substituting sucrose for maltose as the carbon source the cost per liter of the fermentation medium is lowered by a factor of five due to the low price of sucrose compared to maltose.

EXAMPLE VI

As shown in this example, control of concentration of yeast extract provided optimum maltase yield.

Figure 3:
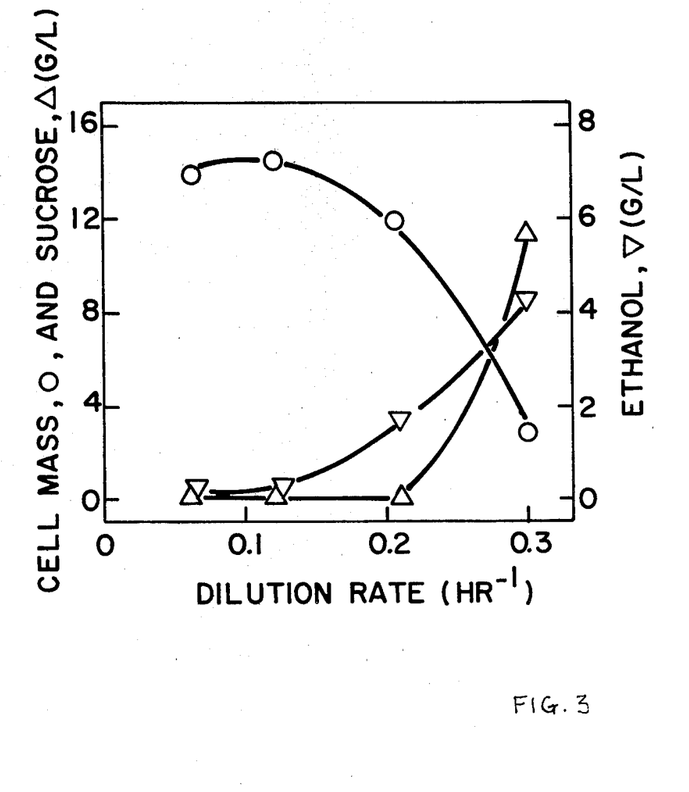
FIG. 3 is a graph of cell mass and activity mass dilution rate for a continuous culture of *S. italicus* 1-4 on sucrose.
Figure 4:
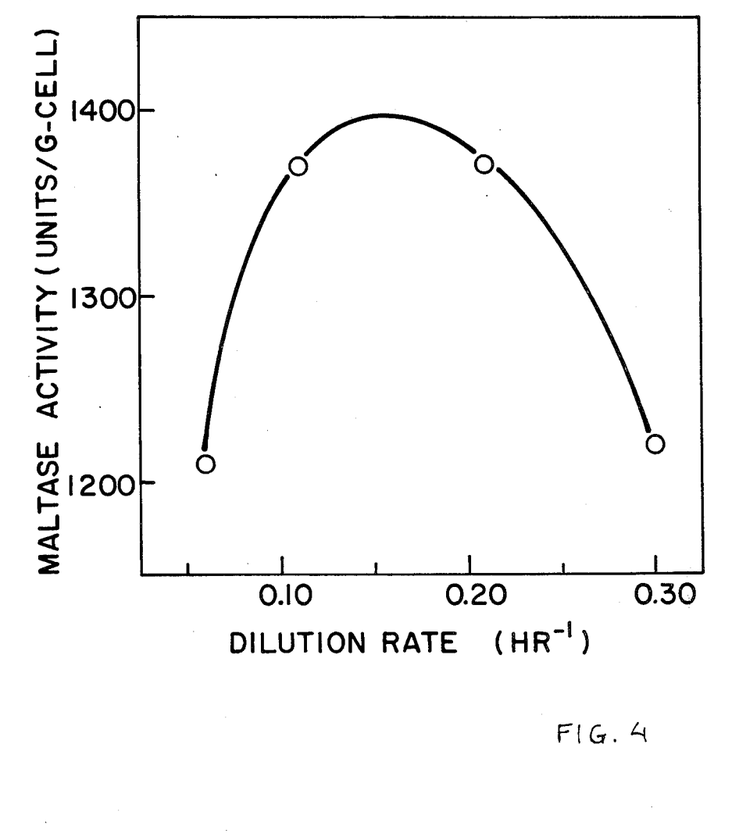
FIG. 4 is a graph of maltase specific activity of *S. italicus* 1-4 as a function of dilution rate.

Strain 1-4 was grown in continuous culture on the mineral salts medium with 30 g/liter of sucrose supplemented with vitamins (μg/liter): 2, folic acid; 400, niacin; and 200 riboflavin. Unlike earlier results in batch culture, yeast extract was not required. The growth in this medium was slow and somewhat unsteady but steady states were eventually established. Cell washout seemed to occur at a lower dilution rate than for the wild type; this corresponds to a lower maximum specific growth rate than observed in batch culture. The cell density, ethanol and residual sucrose concentration profiles are presented in FIG. 3. As shown in FIG. 3, the behavior is similar to that of the wild type; ethanol formation commences at a dilution rate of about 0.2 $h^{-1}$ and cell mass concentration falls. The residual sucrose concentration increases with dilution rate. The relationship between maltase activity and dilution rate is shown in FIG. 4. The characteristic bell-shaped curve is seen with a peak in activity between 0.1 and 0.2 $h^{-1}$. The maximum volumetric productivity again occurs at the same point ($D=0.21$ $h^{-1}$). It appears that maltase expression, even in this constitutive mutant, is still under the dual control of repression and positive growth association. Since it is not known if sucrose actually behaves as an inducer in this system, induction may not be the proper term for this positive growth association. It appears that maltase synthesis is repressed at high dilution rates. The maltase specific activity, although much higher than that obtained from the wild type in continuous culture, was below the maximum value found during batch growth. In fact, the extent to which this activity had been lowered was similar to that observed in the wild type. It appears that many of the same control mechanisms present in the wild type are also active in this mutant.

Figure 5:
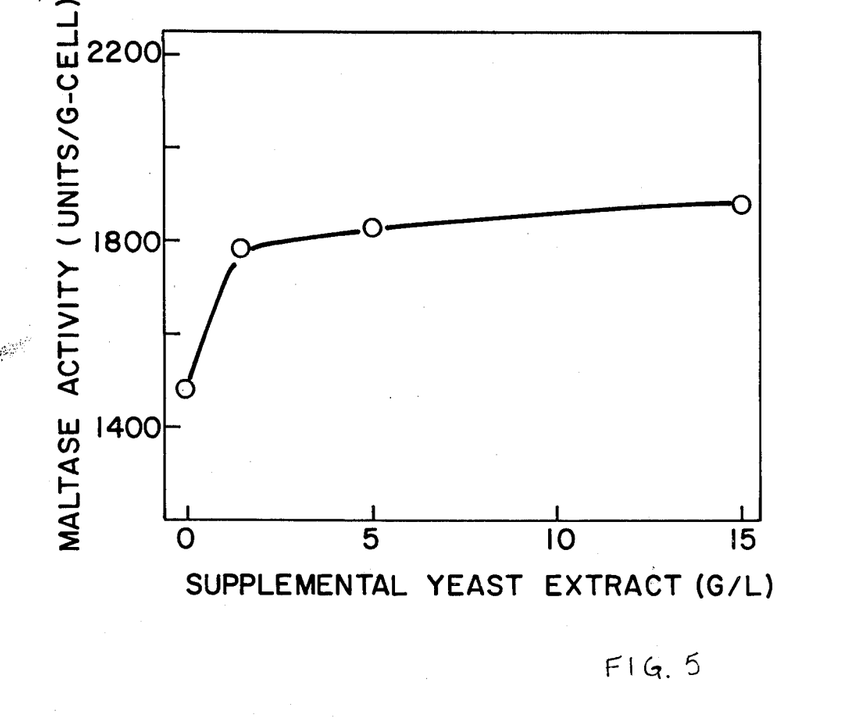
FIG. 5 is a graph of the affect of supplemental yeast extract on maltase specific activity of the continuously cultured constitutive mutant.

Since the addition of yeast extract has a positive effect in batch fermentation, the effects of supplementing the growth medium with it were studied in continuous culture. A constant dilution rate of 0.21 $h^{-1}$ was chosen for this experiment because this represented the point of maximum maltase productivity and specific activity. Steady state maltase activities were then measured as a function of increasing yeast extract concentration, FIG. 5. As shown in FIG. 5, a small supplement of yeast extract causes a sharp jump in maltase activity but increasing amounts have little effect.

By switching to continuous culture from batch the specific productivity was increased 1.7-fold and maximum volumetric productivity by a factor of three to 288 units/g-h and 3420 units l-h, respectively. When the continuous process with strain 1-4 is compared to batch production using the wild type, the improvement is even more impressive. Specific productivity is increased by a factor of four, from 74 to 288 units/g-cell-h, and volumetric productivity goes up eight-fold, from 470 to 3420 units/l-h.

EXAMPLE VII

Figure 6:
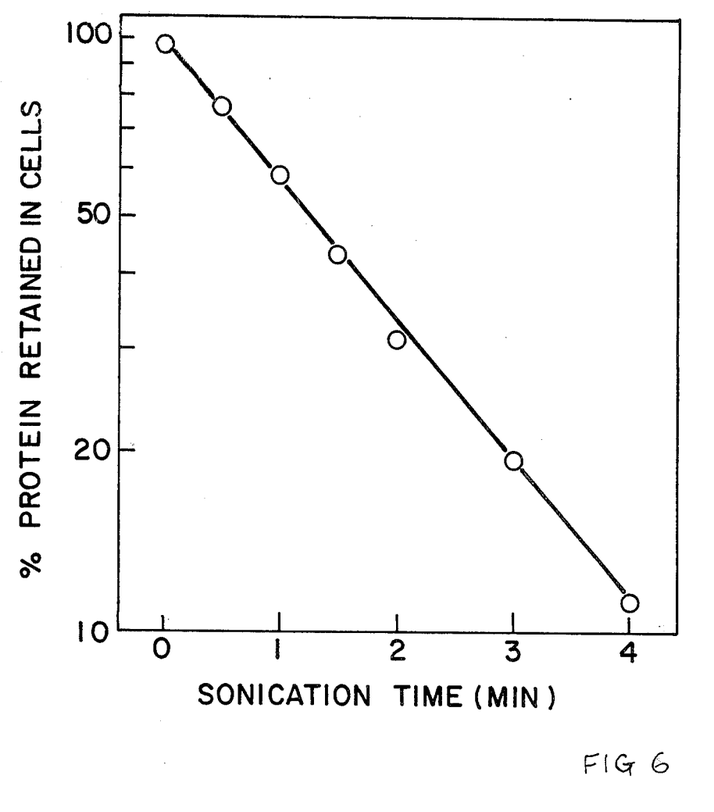
FIG. 6 is a graph of protein release kinetics from *S. italicus* as a function of sonication time.

Since maltase is an intracellular enzyme it is necessary to break open the cells to obtain the enzyme. An ultrasonic cell disrupter, Sonicator Model W-350 (Heat Systems Ultrasonics, Plainview, N.Y.) was used for this purpose. Frozen cell pellets were thawed and resuspended in 10 ml of 1/15 M, pH 6.8, phosphate buffer. The cell suspension was placed in a stainless steel cup suspended in an ice bath. The tip of the sonicator was immersed in the liquid and 100 watts of power at 20 kHz was emitted continuously for variour lengths of time. The acoustic energy is trasmitted to the liquid and disrupts the cells by the mechanical effects of cavitation. The release of protein from the cell is a first-order process wherein the fraction of the total releasable protein retained by the cells (l-x) is given by:

$$(1-x)=e^{-kt}$$

where t is the time of sonication in min and K is the protein release constant in $min^{-1}$. The release constant is a function of the power input and the volume to be sonicated. The kinetics of protein release from S. italicus as a function of sonication time is shown in FIG. 6. The release constant for this system is 0.63 $min^{-1}$.

Figure 7:
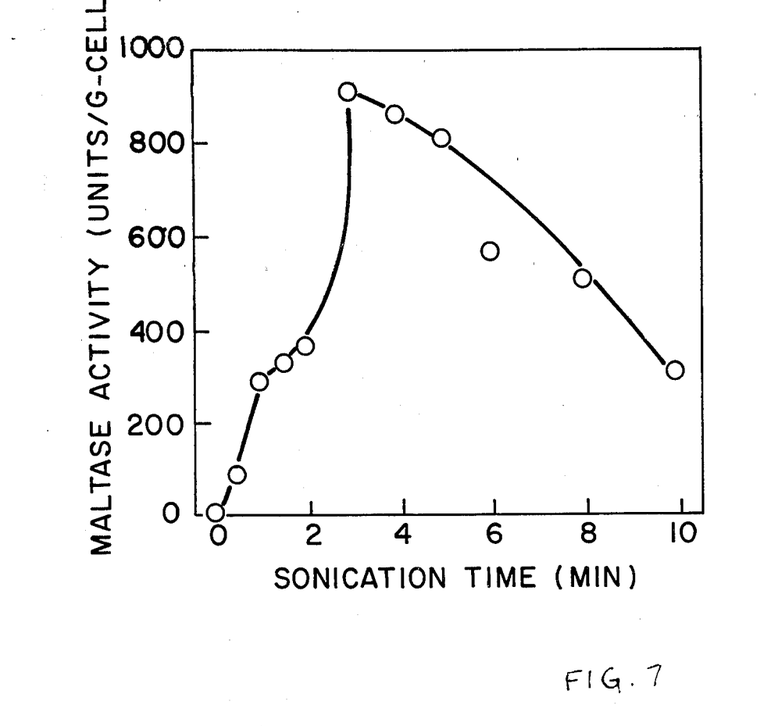
FIG. 7 is a graph of the affect of sonication time on maltase specific activity.

Many enzymes in solution are labile and degrade upon further sonication. The effect of the length of sonication time on maltase specific activity is shown in FIG. 7. The specific activity released exhibits a maximum; if the cells are sonicated too long the enzyme is inactivated. On the other hand, insufficient sonication does not release all of the enzyme. The small shoulder on the front of the peak seems to indicate that a fraction of the enzyme is easier to release. Perhaps some of the enzyme is located in the periplasmic space and the rest is truly intracellular as is the case with invertase. In any case, since the front of the curve is much steeper than the tail, the cells were slightly oversonicated to allow for a slight safety margin. Thus, cell samples were sonicated for four minutes. The cell density seemed to have little effect on the results of the sonication. Finally, sonication was found to be a superior method of releasing maltase when compared to a more traditional method such as decryptification using dimethyl sulfoxide, to permeabilize the cell membrane.

We claim:

1. In a process for forming maltase utilizing Saccharomyces italicus in a growth medium, said Saccharomyces italicus being obtained by mutation of Saccharomyces italicus and having the property of producing maltase while grown on a carbon source selected from the group consisting of maltose, glycerol, acetate, fructose, glucose and sucrose, the improvement which comprises utilizing in the growth medium yeast extract at a concentration of between about 1 and 15 g/L.

2. The process of claim 1 wherein the concentration of yeast extract is between about 2 and 5 g/L.

3. The process of claim 1 wherein the maltase is recovered by sonication of cells of said yeast between about 1 and 6 minutes.

4. The process of claim 1 wherein the sonication time is between about 2 and 4 minutes.

5. The process of claim 1 wherein said growth medium contains sucrose at a concentration between about 5 and 50 g/L.

6. The process of claim 1 wherein the said growth medium contains sucrose at a concentration between about 40 and 45 g/L.

7. The process of any one of claims 1, 2, 3, 4, 5 or 6 wherein the growth medium is continuously added to said *Saccharomyces italicus* in a growth vessel and removing *Saccharomyces italicus* containing maltase for said culture vessel.

8. The process of any one of claims 1, 2, 3, 4, 5 or 6 wherein said Saccharomyces italicus is *Saccharomyces italicus* ATCC 20601.

* * * * *